(12) United States Patent
Audousset

(10) Patent No.: US 6,692,540 B1
(45) Date of Patent: Feb. 17, 2004

(54) DYEING COMPOSITION CONTAINING A PYRAZOLO-[1,5-A]PYRIMIDINE AS OXIDATION BASE AND A PYRIDINE COUPLING AGENT, AND DYEING METHOD

(75) Inventor: Marie-Pascale Audousset, Asnières (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/485,914

(22) PCT Filed: Jun. 2, 1999

(86) PCT No.: PCT/FR99/01294

§ 371 (c)(1),
(2), (4) Date: Apr. 26, 2000

(87) PCT Pub. No.: WO99/66894

PCT Pub. Date: Dec. 29, 1999

(30) Foreign Application Priority Data

Jun. 19, 1998 (FR) ............................................. 98 07797

(51) Int. Cl.$^7$ ................................................. A61K 7/13
(52) U.S. Cl. ................................... 8/409; 8/407; 8/423
(58) Field of Search .............................. 8/407, 409, 423

(56) References Cited

U.S. PATENT DOCUMENTS

| 4,473,375 | A | * | 9/1984 | Clausen | 8/409 |
| 4,487,607 | A | * | 12/1984 | Rose et al. | 8/409 |
| 4,661,114 | A | * | 4/1987 | Konrad et al. | 8/409 |
| 4,713,080 | A | * | 12/1987 | Konrad et al. | 8/409 |
| 4,838,893 | A | * | 6/1989 | Rose et al. | 8/409 |
| 5,082,467 | A | * | 1/1992 | Tamura et al. | 8/409 |
| 5,234,818 | A | * | 8/1993 | Zimmermann et al. | 435/28 |
| 5,378,244 | A | * | 1/1995 | Tamura et al. | 8/409 |
| 5,380,340 | A | | 1/1995 | Neunhoeffer et al. | 8/409 |
| 5,494,490 | A | | 2/1996 | Audousset et al. | 8/409 |
| 5,514,188 | A | | 5/1996 | Cotteret et al. | 8/412 |
| 6,099,593 | A | * | 8/2000 | Terranova et al. | 8/409 |

FOREIGN PATENT DOCUMENTS

| DE | 4029324 | 3/1992 |
| DE | 4133957 | 4/1993 |
| EP | 0599703 | 6/1994 |
| EP | 0634164 | 1/1995 |
| FR | 2586913 | 3/1987 |
| FR | 2750048 | 12/1997 |
| FR | 2771631 | * 6/1999 |
| WO | WO 92/04883 | 4/1992 |
| WO | WO 97/35550 | 10/1997 |
| WO | WO 97/49378 | 12/1997 |
| WO | WO 98/51268 | 11/1998 |
| WO | WO 98/55083 | 12/1998 |

OTHER PUBLICATIONS

Derwent Abstract of FR 2586913, Mar. 1987.
Derwent Abstract of FR 2750048, Dec. 1997.
Derwent Abstract of DE 4029324, Mar. 19, 1992.

* cited by examiner

*Primary Examiner*—Margaret Einsmann
(74) *Attorney, Agent, or Firm*—Finnegan, Henderson, Farabow, Garrett & Dunner, LLP

(57) ABSTRACT

A subject-matter of the invention is a composition for the oxidation dyeing of keratinous fibers comprising at least one pyrazolo[1,5-a]pyrimidine as oxidation base and at least one pyridine coupler, and the oxidation dyeing process employing thus composition.

18 Claims, No Drawings

DYEING COMPOSITION CONTAINING A PYRAZOLO-[1,5-A]PYRIMIDINE AS OXIDATION BASE AND A PYRIDINE COUPLING AGENT, AND DYEING METHOD

A subject-matter of the invention is a composition for the oxidation dyeing of keratinous fibres comprising at least one pyrazolo[1,5-a]pyrimidine as oxidation base and at least one pyridine coupler, and the oxidation dyeing process employing this composition.

It is known to dye keratinous fibres and in particular human hair with dyeing compositions comprising oxidation dye precursors, in particular ortho- or para-phenylenediamines, ortho- or para-aminopnenols, bisphenylalkylenediamines or, alternatively, heterocyclic compounds, generally known as oxidation bases. Oxidation dye precursors or oxidation bases are colourless or weakly coloured compounds which, in combination with oxidizing substances, can give rise by an oxidative coupling process to coloured and colouring compounds.

It is also known that the shades obtained with these oxidation bases can be varied by combining them with couplers or colouring modifiers, the latter being chosen in particular from aromatic meta-diamines, meta-aminophenols, meta-diphenols and certain heterocyclic compounds.

The variety of the molecules employed as oxidation bases and couplers makes it possible to obtain a rich palette of colours.

The so-called "permanent" colouring obtained by virtue of these oxidation dyes has, however, to satisfy a certain number of requirements. Thus, it must have no disadvantages with regard to toxicology and it must make it possible to obtain shades with the desired intensity and behave well in the face of external agents (light, bad weather, washing, permanent waving, perspiration or rubbing).

The dyes must also make it possible to cover white hair and, finally, be as unselective as possible, that is to say make it possible to obtain the least possible differences in colouring along the same keratinous fibre, this being because the latter can be sensitized (i.e. damaged) to a varying degree between its tip and its root.

Provision has already been made, in particular in Patent Application FR-A-2,750,048, for the use of pyrazolo[1,5-a]pyrimidines as oxidation base, alone or in combination with one or more couplers. However, the colourings obtained are not always powerful enough, chromatic enough or sufficiently resistant to the various attacks which hair may be subjected to.

In point of fact, the Applicant Company has now just discovered, entirely unexpectedly and surprisingly, that the combination of the pyrazolo[1,5-a]pyrimidines of formula (I) defined hereinbelow and of at least one pyridine coupler of formula (II) defined hereinbelow made it possible to obtain powerful colourings furthermore exhibiting improved properties of resistance with respect to various attacks which hair may be subjected to (shampoos, light, bad weather, permanent waves, perspiration, rubbing and the like).

These discoveries form the basis of the present invention.

A first subject-matter of the invention is therefore a composition for the oxidation dyeing of keratinous fibres and in particular of human keratinous fibres, such as hair, characterized in that it comprises, in a medium appropriate for dyeing:

at least one oxidation base chosen from pyrazolo[1,5-a] pyrimidines of following formula (I) and their addition salts with an acid or with a base:

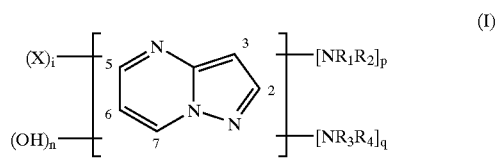

in which:

$R_1$, $R_2$, $R_3$ and $R_4$, which are identical or different, denote a hydrogen atom, a $(C_1-C_4)$alkyl radical, an aryl radical, a hydroxy$(C_1-C_4)$alkyl radical, a polyhydroxy $(C_2-C_4)$alkyl radical, a $(C_1-C_4)$alkoxy$(C_1-C_4)$alkyl radical, an amino$(C_1-C_4)$alkyl radical (it being possible for the amine to be protected by an acetyl, an amido or a sulphonyl), a $(C_1-C_4)$alkylamino$(C_1-C_4)$alkyl radical, a di[$(C_1-C_4)$alkyl]amino$(C_1-C_4)$alkyl radical (it being possible for the dialkyls to form a 5- or 6-membered aliphatic or heterocyclic ring), a hydroxy $(C_1-C_4)$alkylamino$(C_1-C_4)$alkyl radical or a di[hydroxy$(C_1-C_4)$alkyl]amino$(C_1-C_4)$alkyl radical;

the X radicals, which are identical or different, denote a hydrogen atom, a $(C_1-C_4)$alkyl radical, an aryl radical, a hydroxy$(C_1-C_4)$alkyl radical, a polyhydroxy$(C_2-C_4)$ alkyl radical, an amino$(C_1-C_4)$alkyl radical, a $(C_1-C_4)$ alkylamino$(C_1-C_4)$alkyl radical, a di[$(C_1-C_4)$alkyl] amino$(C_1-C_4)$alkyl radical (it being possible for the dialkyls to form a 5- or 6-membered aliphatic or heterocyclic ring), a hydroxy$(C_1-C_4)$alkylamino $(C_1-C_4)$alkyl radical, a di[hydroxy$(C_1-C_4)$alkyl]amino $(C_1-C_4)$alkyl radical, an amino radical, a $(C_1-C_4)$ alkylamino radical, a di[$(C_1-C_4)$alkyl]amino radical, a halogen atom, a carboxylic acid group or a sulphonic acid group;

i has the value 0, 1, 2 or 3;

p has the value 0 or 1;

q has the value 0 or 1;

n has the value 0 or 1;

with the proviso that:

(i) the sum p+q is other than 0;

(ii) when p+q is equal to 2, then n has the value 0 and the $NR_1R_2$ and $NR_3R_4$ groups occupy the (2,3), (5,6), (6,7), (3,5) or (3,7) positions;

(iii) when p+q is equal to 1, then n has the value 1 and the $NR_1R_2$ (or $NR_3R_4$) group and the OH group occupy the (2,3), (5,6), (6,7), (3,5) or (3,7) positions;

and at least one coupler chosen from pyridines of following formula (II) and their addition salts with an acid:

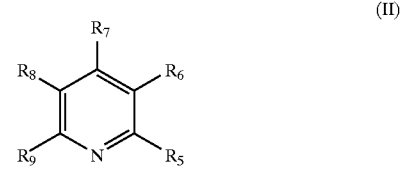

in which:

$R_5$ represents a hydrogen atom or a hydroxyl, amino, $(C_1-C_4)$alkoxy, mono- or di$(C_1-C_4)$alkylamino, monohydroxy$(C_1-C_4)$alkylamino, polyhydroxy $(C_2-C_4)$alkylamino, monohydroxy$(C_1-C_4)$alkoxy, polyhydroxy$(C_2-C_4)$alkoxy or monohydroxy$(C_1-C_4)$ alkoxy$(C_1-C_4)$alkoxy radical;

$R_6$ represents a hydrogen atom or a hydroxyl, amino or $(C_1-C_4)$alkyl radical;

$R_7$ represents a hydrogen atom or a $(C_1-C_4)$alkyl radical;

$R_8$ represents a hydrogen or halogen atom, such as chlorine, bromine, iodine or fluorine, or an amino radical;

$R_9$ represents a hydrogen atom or a hydroxyl, amino, $(C_1-C_4)$alkoxy, monohydroxy$(C_1-C_4)$alkoxy or polyhydroxy$(C_2-C_4)$alkoxy radical; at least two of the $R_5$ to $R_9$ radicals being other than a hydrogen atom, and the said composition being devoid of any enzymatic system capable of bringing about oxidation of the compounds of formula (I) and/or (II).

As indicated above, the dyeing composition in accordance with the invention results in powerful colourings which furthermore exhibit excellent properties of resistance with respect to the action of various external agents (light, bad weather, washing, permanent waving, perspiration or rubbing).

Another subject-matter of the invention is a process for the oxidation dyeing of keratinous fibres employing this dyeing composition.

The pyrazolo[1,5-a]pyrimidies of formula (I) which can be used as oxidation base in the dyeing composition in accordance with the invention are known compounds which are disclosed in Patent Application FR-A-2,750,048.

Mention may in particular be made, among the pyrazolo [1,5-a]pyrimidines of formula (I) which can be used as oxidation base in the dyeing compositions in accordance with the invention, of:

pyrazolo[1,5-a]pyrimidine-3,7-diamine;

2-methylpyrazolo[1,5-a]pyrimidine-3,7-diamine;

2,5-dimethylpyrazolo[1,5-a]pyrimidine-3,7-diamine;

pyrazolo[1,5-a]pyrimidine-3,5-diamine;

2,7-dimethylpyrazolo[4,5-a]pyrimidine-3,5-diamine;

3-aminopyrazolo[1,5-a]pyrimidin-7-ol;

3-amino-5-methylpyrazolo[1,5-a]pyrimidin-7-ol;

3-aminopyrazolo[1,5-a]pyrimidin-5-ol;

2-(3-aminopyrazolo[1,5-a]pyrimidin-7-ylamino)ethanol;

3-amino-7-(β-hydroxyethylamino)-5-methylpyrazolo[1,5-a]pyrimidine;

2-(7-aminopyrazolo[1,5-a]pyrimidin-3-ylamino)ethanol;

2-[(3-aminopyrazolo[1,5-a]pyrimidin-7-yl)(2-hydroxyethyl)amino]ethanol;

2-[(7-aminopyrazolo[1,5-a]pyrimidin-3-yl)(2-hydroxyethyl)amino]ethanol;

5,6-dimethylpyrazolo[1,5-a]pyrimidine-3,7-diamine;

2,6-dimethylpyrazolo[1,5-a]pyrimidine-3,7-diamine;

2,5,N-7,N-7-tetramethylpyrazolo[1,5-a]pyrimidine-3,7-diamine;

and their addition salts with an acid or with a base.

Mention may in particular be made, among the pyridines of formula (II) which can be used as coupler in the dyeing compositions in accordance with the invention, of:

2,6-dihydroxy-3,4-dimethylpyridine, 5-chloro-2,3-dihydroxypyridine, 3,5-diamino-2,6-dimethoxypyridine, 3-amino-2-(β-hydroxyethyl)amino-6-methoxypyridine, 2,6-bis(β-hydroxyethyloxy)-3,5-diaminopyridine, 3-amino-5-hydroxy-2,6-dimethoxypyridine, 3-amino-2-methylamino-6-methoxypyridine, 2-amino-3-hydroxypyridine, 2-dimethylamino-5-aminopyridine, 2,6-diaminopyridine, 3,5-diamino-2-(β,γ-dihydroxypropyloxy)pyridine, 3,5-diamino-2-(γ-hydroxypropyloxyethyloxy)pyridine, and their addition salts with an acid.

Generally, the addition salts with an aid which can be used in the context of the invention (oxidation bases and couplers) are chosen in particular from hydrochlorides, hydrobromides, sulphates, citrates, succinates, tartrates, lactates and acetates. The addition salts with a base which can be used in the context of the dyeing compositions of the invention are in particular hose obtained with sodium hydroxide, potassium hydroxide, aqueous ammonia or amines.

The pyrazolo[1,5-a]pyrimidine or pyrazolo[1,5-a] pyrimidines of formula (I) in accordance with the invention and/or the addit on salt or their addition salts with an acid or with a base preferably represent from 0.0005 to 12% by weight approximately of the total weight of the dyeing composition and more preferably still from 0.005 to 6% by weight approximately of this weight.

The pyridine or pyridines of formula (II) in accordance with the invention and/or the addition salt or their addition salts with an acid preferably represent from 0.0001 to 10% by weight approximately of the total weight of the dyeing composition and more preferably still from 0.005 to 5% by weight approximately of this weight.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of $C_1-C_4$ alkanols, such as ethanol and isopropanol; glycerol; glycols and glycol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 2 approximately and preferably between 5 and 11 approximately. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of example, of aqueous ammonia, alkaline carbonates, alkanolamines, such as mono-, di- and triethanolamines, 2-methyl-2-aminopropanol and their derivatives, sodium hydroxide, potassium hydroxide and the compounds or following formula (III):

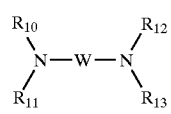

(III)

in which W is a propylene residue optionally substituted by a hydroxyl group or a $(C_1-C_6)$alkyl radical and $R_{10}$, $R_{11}$, $R_{12}$ and $R_{13}$, which are identical or different, represent a hydrogen atom or a $(C_1-C_6)$alkyl or hydroxy$(C_1-C_6)$alkyl radical.

The dyeing composition in accordance with the invention can also comprise at least one direct dye, in particular for modifying the shades or enriching them with highlights.

The dyeing composition in accordance with the invention can also include various adjuvants conventionally used in hair dyeing compositions, such as anionic, cationic, non-ionic, amphoteric or zwitterionic surface-active agents or their mixtures, anonic, cationic, non-ionic, amphoteric or zwitterionic polymers or their mixtures, inorganic or organic thickening agents, such as, for example, non-ionic guar gums, antioxidizing agents, penetration agents, sequestering agents, fragrances, buffers, dispersing agents, conditioning agents, such as, or example, volatile or nonvolatile and modified or unmodified silicones, film-forming agents, ceramides, preserving agents or opacifying agents.

Of course, a person skilled in the art will take care to choose this or these optional additional compound or compounds so that the advantageous properties intrinsically attached to the oxidation dyeing composition in accordance with the invention are not, or not substantially, detrimentally affected by the envisaged addition or additions.

The dyeing composition in accordance with the invention can be provided in various forms, such as in the form of liquids, powders, creams or gels, or in any other form appropriate for carrying out dyeing of keratinous fibres and in particular human hair.

Another subject-matter of the invention is a process for the oxidation dyeing of keratinous fibres and in particular human keratinous fibres, such as hair, employing the dyeing composition as defined above.

According to this process, at least one dyeing composition as defined above is applied to the fibres, the colour being developed at acidic, neutral or alkaline pH using a non-enzymatic oxidizing agent which is added only at the time of use to the dyeing composition or which is present in an oxidizing composition applied simultaneously or sequentially.

According to a preferred embodiment of the dyeing process or the invention, the dyeing composition described above is preferably mixed, at the time of use, with an oxidizing composition comprising, in a medium appropriate for dyeing, at least one non-enzymatic oxidizing agent present in an amount sufficient to develop a colouring. The mixture obtained is subsequently applied to the keratinous fibres and is left to stand for 3 to 50 minutes approximately, preferably 5 to 30 minutes approximately, after which the hair is rinsed, washed with a shampoo, rinsed again and dried.

The oxidizing agent present in the oxidizing composition as defined above can be chosen from oxidizing agents conventionally used for the oxidation dyeing of keratinous fibres and among which may be mentioned hydrogen peroxide, urea hydrogen peroxide, alkali metal bromates, peracids and persalts, such as perborates and persulphates. Hydrogen peroxide is particularly preferred.

The pH of the oxidizing composition including the oxidizing agent as defined above is such that, after mixing with the dyeing composition, the pH of the resulting composition applied to keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels, or in any other form appropriate or carrying out dyeing of keratinous fibres and in particular of human hair.

Another subject-matter of the invention is a dyeing multi-compartment device or kit or any other packaging system with several compartments, a first compartment of which includes the dyeing composition as defined above and a second compartment of which includes the oxidizing composition as defined above. These devices can be equipped with a means allowing the desired mixture to be deposited on the hair, such as the devices disclosed in Patent FR-2,586,913 on behalf of the Applicant Company.

The following examples are intended to illustrate the invention without, however, exhibiting a limiting nature.

EXAMPLES

Dying Examples 1 to 3 in Alkaline Medium

The following dyeing compositions in accordance with the invention were prepared (contents in grams):

| EXAMPLE | 1 | 2 | 3 |
|---|---|---|---|
| 3,7-Diaminopyrazolopyrimidine.2HCl (oxidation base of formula (I)) | 0.666 | 0.666 | 0.666 |
| 2-Amino-3-hydroxypyridine (coupler of formula (II)) | 0.333 | — | — |
| 2,6-Diaminopyridine (coupler of formula (II)) | — | 0.333 | — |
| 3,5-Diamino-2-(γ-hydroxypropyloxy-ethyloxy)pyridine.2HCl (coupler of formula (II)) | — | — | 0.858 |
| Common dyeing vehicle No. 1 | (*) | (*) | (*) |
| Demineralized water, q.s. for | 100 g | 100 g | 100 g |

(*)Common dyeing vehicle No. 1:

| | |
|---|---|
| 96° alcohol | 18 g |
| Sodium metabisulphite as a 35% aqueous solution | 0.68 g |
| Pentasodium salt of diethylenetriamine-pentaacetic acid | 1.1 g |
| Aqueous ammonia comprising 20% of $NH_3$ | 10.0 g |

At the time of use, each of the above dyeing compositions was mixed, weight for weight, with a 20-volume hydrogen peroxide solution (6% by weight) of pH 3.

The mixture obtained was applied to locks of natural grey hair comprising 90% of white hairs for 30 minutes. The locks were subsequently rinsed, washed with a standard shampoo, rinsed again and then dried.

The shades obtained appear in the table below:

| EXAMPLE | Dyeing pH | Shade obtained |
|---|---|---|
| 1 | 10 ± 0.2 | Iridescent ash red |
| 2 | 10 ± 0.2 | Deep purple red |
| 3 | 10 ± 0.2 | Deep purple red |

Dying Examples 4 to 6 in Neutral Medium

The following dyeing compositions in accordance with the invention were prepared (contents in grams):

| EXAMPLE | 4 | 5 | 6 |
|---|---|---|---|
| 3,7-Diaminopyrazolopyrimidine.2HCl (oxidation base of formula (I)) | 0.666 | 0.666 | 0.666 |
| 2,6-Dihydroxy-4-methylpyridine (coupler of formula (II)) | 0.345 | — | — |
| 2,6-Dihydroxy-3,4-dimethylpyridine (coupler of formula (II)) | — | 0.417 | — |
| 3,5-Diamino-2-(β,γ-dihydroxypropyl-oxy)pyridine.2HCl (coupler of formula (II)) | — | — | 0.816 |
| Common dyeing vehicle No. 2 | () | () | (**) |
| Demineralized water, q.s. for | 100 g | 100 g | 100 g |

(**)Common dyeing vehicle No. 2:
| | |
|---|---|
| 96° Ethanol | 18 g |
| K$_2$HPO$_4$/KH$_2$PO$_4$ (1.5M/1M) buffer | 0.68 g |
| Sodium metabisulphite | 0.68 g |
| Pentasodium salt of diethylenetriamine-pentaacetic acid | 1.1 g |

At the time of use, each of the above dyeing compositions was mixed, weight for weight, with a 20-volume hydrogen peroxide solution (6% by weight) of pH 3.

The mixture obtained was applied to locks of natural grey hair comprising 90% of white hairs for 30 minutes. The locks were subsequently rinsed, washed with a standard shampoo, rinsed again and then dried.

The shades obtained appear in the table below:

| EXAMPLE | Dyeing pH | Shade obtained |
|---|---|---|
| 4 | 5.7 ± 0.2 | Iridescent ash red |
| 5 | 5.7 ± 0.2 | Iridescent |
| 6 | 5.7 ± 0.2 | Deep purple red |

What is claimed is:

1. A dyeing kit having at least two compartments, wherein a first compartment contains a dyeing composition and a second compartment contains an oxidizing composition comprising a non-enzymatic oxidizing agent, wherein said at least one dyeing composition comprises at least one oxidation base chosen from pyrazolo[1,5-a]pyrimidines of formula (I) and acid and base addition salts thereof:

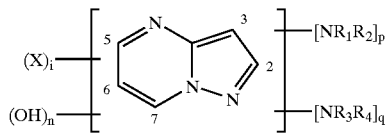

in which:

$R_1$, $R_2$, $R_3$ and $R_4$, each of which may be identical or different, are chosen from a hydrogen atom; ($C_1$–$C_4$) alkyl radicals; aryl radicals; hydroxy($C_1$–$C_4$)alkyl radicals; polyhydroxy($C_2$–$C_4$)alkyl radicals; ($C_1$–$C_4$) alkoxy($C_1$–$C_4$)alkyl radicals; amino($C_1$–$C_4$)alkyl radicals in which the amine is optionally protected by an acetyl, an amido or a sulphonyl group; ($C_1$–$C_4$) alkylamino($C_1$–$C_4$)alkyl radicals; di(($C_1$–$C_4$)alkyl)amino($C_1$–$C_4$)alkyl radicals in which the dialkyls optionally form 5- or 6-member aliphatic or heterocyclic rings; hydroxy($C_1$–$C_4$)alkylamino($C_1$–$C_4$)alkyl radicals; and di(hydroxy($C_1$–$C_4$)alkyl)amino($C_1$–$C_4$) alkyl radicals;

the X radicals, each of which may be identical or different, are chosen from a hydrogen atom; ($C_1$–$C_4$)alkyl radicals; aryl radicals; hydroxy($C_1$–$C_4$)alkyl radicals; polyhydroxy($C_2$–$C_4$)alkyl radicals; amino($C_1$–$C_4$)alkyl radicals; ($C_1$–$C_4$)alkylamino($C_1$–$C_4$)alkyl radicals; di(($C_1$–$C_4$)alkyl)amino($C_1$–$C_4$)alkyl radicals in which the dialkyls optionally form 5- or 6-member aliphatic or heterocyclic rings; hydroxy($C_1$–$C_4$)alkylamino ($C_1$–$C_4$)alkyl radicals; di(hydroxy($C_1$–$C_4$)alkyl)amino ($C_1$–$C_4$)alkyl radicals; amino radicals; ($C_1$–$C_4$) alkylamino radicals; di(($C_1$–$C_4$)alkyl)amino radicals; halogen atoms; carboxylic acid groups; and sulphonic acid groups;

i is 0, 1, 2 or 3;

p is 0 or 1;

q is 0 or 1;

n is 0 or 1;

with the proviso that:

the sum p+q equals a value other than 0;

when p+q equals 2, then n is 0, and the NR$_1$R$_2$ and NR$_3$R$_4$ groups occupy the (2,3), (5,6), (6,7), (3,5) or (3,7) positions;

when p+q equals 1, then n is 1, and the NR$_1$R$_2$ group or NR$_3$R$_4$ group and the OH group occupy the (2,3), (5,6), (6,7), (3,5) or (3,7) positions; and at least one coupler chosen from substituted pyridines of formula (II) and acid addition salts thereof:

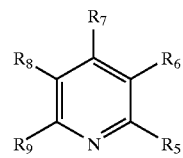

in which:

$R_5$ is chosen from a hydrogen atom, a hydroxyl radical, an amino radical, a ($C_1$–$C_4$)alkoxy radicals, mono($C_1$–$C_4$) alkylamino radicals, di($C_1$–$C_4$)alkylamino radicals, monohydroxy($C_1$–$C_4$)alkylamino radicals, polyhydroxy($C_2$–$C_4$)alkylamino radicals, monohydroxy($C_1$–$C_4$)alkoxy radicals, polyhydroxy ($C_2$–$C_4$)alkoxy radicals, and monohydroxy($C_1$–$C_4$) alkoxy($C_1$–$C_4$)alkoxy radicals;

$R_6$ is chosen from a hydrogen atom, a hydroxyl radical, an amino radical, and ($C_1$–$C_4$)alkyl radicals;

$R_7$ is chosen from a hydrogen atom and ($C_1$–$C_4$)alkyl radicals;

$R_8$ is chosen from a hydrogen atom, iodine, fluorine, and an amino radical;

$R_9$ is chosen from a hydrogen atom, a hydroxyl radical, an amino radical, ($C_1$–$C_4$)alkoxy radicals, monohydroxy ($C_1$–$C_4$)alkoxy radicals, and polyhydroxy($C_2$–$C_4$) alkoxy radicals;

wherein at least two of the radicals $R_5$ to $R_9$ are at least one substituent other than a hydrogen atom, wherein the at least one coupler is not 2,5-diaminopyridine; and wherein said composition lacks any enzymatic system capable of oxidizing any of the compounds of formula (I) and/or (II).

2. A composition for the oxidation dyeing of keratinous fibers comprising:

at least one oxidation base chosen from pyrazolo[1,5-a]pyrimidines of formula (I) and acid and base addition salts thereof:

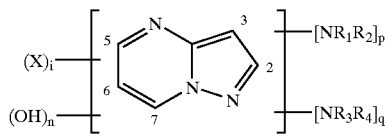

in which:

$R_1$, $R_2$, $R_3$ and $R_4$, each of which may be identical or different, are chosen from a hydrogen atom; ($C_1$–$C_4$) alkyl radicals; aryl radicals; hydroxy($C_1$–$C_4$)alkyl radicals; polyhydroxy($C_2$–$C_4$)alkyl radicals; ($C_1$–$C_4$) alkoxy($C_1$–$C_4$)alkyl radicals; amino($C_1$–$C_4$)alkyl radicals in which the amine is optionally protected by an acetyl, an amido or a sulphonyl group; ($C_1$–$C_4$) alkylamino($C_1$–$C_4$)alkyl radicals; di(($C_1$–$C_4$)alkyl) amino($C_1$–$C_4$)alkyl radicals in which the dialkyls optionally form 5- or 6-member aliphatic or heterocyclic rings; hydroxy($C_1$–$C_4$)alkylamino($C_1$–$C_4$)alkyl radicals; and di(hydroxy($C_1$–$C_4$)alkyl)amino($C_1$–$C_4$) alkyl radicals;

the X radicals, each of which may be identical or different, are chosen from a hydrogen atom; ($C_1$–$C_4$)alkyl radicals; aryl radicals; hydroxy($C_1$–$C_4$)alkyl radicals; polyhydroxy($C_2$–$C_4$)alkyl radicals; amino($C_1$–$C_4$)alkyl radicals; ($C_1$–$C_4$)alkylamino($C_1$–$C_4$)alkyl radicals; di(($C_1$–$C_4$)alkyl)amino($C_1$–$C_4$)alkyl radicals in which the dialkyls optionally form 5- or 6-member aliphatic or heterocyclic rings; hydroxy($C_1$–$C_4$)alkylamino ($C_1$–$C_4$)alkyl radicals; di(hydroxy($C_1$–$C_4$)alkyl)amino ($C_1$–$C_4$)alkyl radicals; amino radicals; ($C_1$–$C_4$) alkylamino radicals; di(($C_1$–$C_4$)alkyl)amino radicals; halogen atoms; carboxylic acid groups; and sulphonic acid groups;

i is 0, 1, 2 or 3;

p is 0 or 1;

q is 0 or 1;

n is 0 or 1;

with the proviso that:

the sum p+q equals a value other than 0;

when p+q equals 2, then n is 0, and the $NR_1R_2$ and $NR_3R_4$ groups occupy the (2,3), (5,6), (6,7), (3,5) or (3,7) positions;

when p+q equals 1, then n is 1, and the $NR_1R_2$ group or $NR_3R_4$ group and the OH group occupy the (2,3), (5,6), (6,7), (3,5) or (3,7) positions; and at least one coupler chosen from substituted pyridines of formula (II) and acid addition salts thereof:

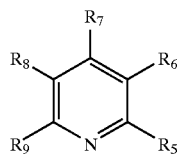

in which $R_5$ is chosen from a hydrogen atom, a hydroxyl radical, an amino radical, ($C_1$–$C_4$)alkoxy radicals, mono($C_1$–$C_4$) alkylamino radicals, di($C_1$–$C_4$)alkylamino radicals, monohydroxy($C_1$–$C_4$)alkylamino radicals, polyhydroxy($C_2$–$C_4$)alkylamino radicals, monohydroxy($C_1$–$C_4$)alkoxy radicals, polyhydroxy ($C_2$–$C_4$)alkoxy radicals, and monohydroxy($C_1$–$C_4$) alkoxy($C_1$–$C_4$)alkoxy radicals;

$R_6$ is chosen from a hydrogen atom, a hydroxyl radical, an amino radical, and ($C_1$–$C_4$)alkyl radicals;

$R_7$ is chosen from a hydrogen atom and ($C_1$–$C_4$)alkyl radicals;

$R_8$ is chosen from a hydrogen atom, iodine, fluorine, and an amino radical;

$R_9$ is chosen from a hydrogen atom, a hydroxyl radical, an amino radical, ($C_1$–$C_4$)alkoxy radicals, monohydroxy ($C_1$–$C_4$)alkoxy radicals, and polyhydroxy($C_2$–$C_4$) alkoxy radicals;

wherein at least two of the radicals $R_5$ to $R_9$ are at least one substituent other than a hydrogen atom, wherein the at least one coupler is not 2,5-diaminopyridine; and wherein said composition lacks any enzymatic system capable of oxidizing any of the compounds of formula (I) and/or (II).

3. A composition according to claim 2, wherein said keratinous fibers are human keratinous fibers.

4. A composition according to claim 3, wherein said human keratinous fibers are hairs.

5. A composition according to claim 2, wherein said pyrazolo-[1,5-a]pyrimidines of formula (I) are chosen from:

pyrazolo[1,5-a]pyrimidine-3,7-diamine;

2-methylpyrazolo[1,5-a]pyrimidine-3,7-diamine;

2,5-dimethylpyrazolo[1,5-a]pyrimidine-3,7-diamine;

pyrazolo[1,5-a]pyrimidine-3,5-diamine;

2,7-dimethylpyrazolo[1,5-a]pyrimidine-3,5-diamine;

3-aminopyrazolo[1,5-a]pyrimidin-7-ol;

3-amino-5-methylpyrazolo[1,5-a]pyrimidin-7-ol;

3-aminopyrazolo[1,5-a]pyrimidin-5-ol;

2-(3-aminopyrazolo[1,5-a]pyrimidin-7-ylamino)ethanol;

3-amino-7-(β-hydroxyethylamino)-5-methylpyrazolo[1,5-a]pyrimidine;

2-(7-aminopyrazolo[1,5-a]pyrimidin-3-ylamino)ethanol;

2-[(3-aminopyrazolo[1,5-a]pyrimidin-7-yl)(2-hydroxyethyl)amino]ethanol;

2-[(7-aminopyrazolo[1,5-a]pyrimidin-3-yl)(2-hydroxylethyl)amino]ethanol;

5,6-dimethylpyrazolo[1,5-a]pyrimidine-3,7-diamine;

2,6-dimethylpyrazolo[1,5-a]pyrimidine-3,7-diamine;

2,5,N-7,N-7-tetramethylpyrazolo[1,5-a]pyrimidine-3,7-diamine;

and acid and base addition salts thereof.

6. A composition according to claim 2, wherein said substituted pyridines of formula (II) are chosen from:

2,6-dihydroxy-3,4-dimethylpyridine;

3,5-diamino-2,6-dimethoxypyridine;

3-amino-2-(β-hydroxyethyl)amino-6-methoxypyridine;

2,6-bis(β-hydroxyethyloxy)-3,5-diaminopyridine;

3-amino-5-hydroxy-2,6-dimethoxypyridine;

3-amino-2-methylamino-6-methoxypyridine;

2-amino-3-hydroxypyridine;

2-dimethylamino-5-aminopyridine;

2,6-diaminopyridine;

3,5-diamino-2-(β,γ-dihydroxypropyloxy)pyridine;
3,5-diamino-2-(γ-hydroxypropyloxyethyloxy)pyridine;
and acid addition salts thereof.

7. A composition according to claim 2, wherein said acid addition salts are chosen from hydrochlorides, hydrobromides, sulphates, citrates, succinates, tartrates, lactates, and acetates.

8. A composition according to claim 2, wherein said base addition salts are chosen from those salts obtained with sodium hydroxide, potassium hydroxide, aqueous ammonia, and amines.

9. A composition according to claim 2, wherein said at least one oxidation base is present in an amount ranging from 0.0005 to 12% by weight of the total weight of said composition.

10. A composition according to claim 2, wherein said at least one oxidation base is present in an amount ranging from 0.005 to 6% by weight of the total weight of said composition.

11. A composition according to claim 2, wherein said at least one coupler is present in an amount ranging from 0.0001 to 10% by weight of the total weight of said composition.

12. A composition according to claim 11, wherein said at least one coupler is present in an amount ranging from 0.005 to 5% by weight of the total weight of said composition.

13. A composition according to claim 2, further comprising at least one adjuvant or at least one direct dye.

14. A composition according to claim 2, further comprising water or a mixture of water and at least one organic solvent.

15. A process for the oxidation dyeing of keratinous fibers, comprising:
applying at least one dyeing composition to said fibers; and
developing a color at acidic, neutral or alkaline pH in the presence of a non-enzymatic oxidizing agent,
wherein said oxidizing agent is added to said dyeing composition only at the time of application or is added as part of an oxidizing composition that is applied simultaneously with or sequentially to said dyeing composition; and
wherein said at least one dyeing composition comprises at least one oxidation base chosen from pyrazolo[1,5-a]pyrimidines of formula (I) and acid and base addition salts thereof:

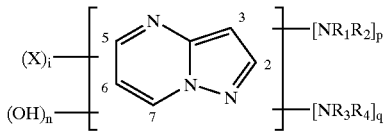

in which:
$R_1$, $R_2$, $R_3$ and $R_4$, each of which may be identical or different, are chosen from a hydrogen atom; $(C_1-C_4)$ alkyl radicals; aryl radicals; hydroxy$(C_1-C_4)$alkyl radicals; polyhydroxy$(C_2-C_4)$alkyl radicals; $(C_1-C_4)$ alkoxy$(C_1-C_4)$alkyl radicals; amino$(C_1-C_4)$alkyl radicals in which the amine is optionally protected by an acetyl, an amido or a sulphonyl group; $(C_1-C_4)$ alkylamino$(C_1-C_4)$alkyl radicals; di$((C_1-C_4)$alkyl) amino$(C_1-C_4)$alkyl radicals in which the dialkyls optionally form 5- or 6-member aliphatic or heterocyclic rings; hydroxy$(C_1-C_4)$alkylamino$(C_1-C_4)$alkyl radicals; and di(hydroxy$(C_1-C_4)$alkyl)amino$(C_1-C_4)$ alkyl radicals;
the X radicals, each of which may be identical or different, are chosen from a hydrogen atom; $(C_1-C_4)$alkyl radi-
cals; aryl radicals; hydroxy$(C_1-C_4)$alkyl radicals; polyhydroxy$(C_2-C_4)$alkyl radicals; amino$(C_1-C_4)$alkyl radicals; $(C_1-C_4)$alkylamino$(C_1-C_4)$alkyl radicals; di$((C_1-C_4)$alkyl)amino$(C_1-C_4)$alkyl radicals in which the dialkyls optionally form 5- or 6-member aliphatic or heterocyclic rings; hydroxy$(C_1-C_4)$alkylamino $(C_1-C_4)$alkyl radicals; di(hydroxy$(C_1-C_4)$alkyl)amino $(C_1-C_4)$alkyl radicals; amino radicals; $(C_1-C_4)$ alkylamino radicals; di$((C_1-C_4)$alkyl)amino radicals; halogen atoms; carboxylic acid groups; and sulphonic acid groups;
i is 0, 1, 2 or 3;
p is 0 or 1;
q is 0 or 1;
n is 0 or 1;
with the proviso that:
the sum p+q equals a value other than 0;
when p+q equals 2, then n is 0, and the $NR_1R_2$ and $NR_3R_4$ groups occupy the (2,3), (5,6), (6,7), (3,5) or (3,7) positions;
when p+q equals 1, then n is 1, and the $NR_1R_2$ group or $NR_3R_4$ group and the OH group occupy the (2,3), (5,6), (6,7), (3,5) or (3,7) positions; and
at least one coupler chosen from substituted pyridines of formula (II) and acid addition salts thereof:

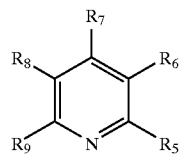

in which:
$R_5$ is chosen from a hydrogen atom, a hydroxyl radical, an amino radical, $(C_1-C_4)$alkoxy radicals, mono$(C_1-C_4)$ alkylamino radicals, di$(C_1-C_4)$alkylamino radicals, monohydroxy$(C_1-C_4)$alkylamino radicals, polyhydroxy$(C_2-C_4)$alkylamino radicals, monohydroxy$(C_1-C_4)$alkoxy radicals, polyhydroxy $(C_2-C_4)$alkoxy radicals, and monohydroxy$(C_1-C_4)$ alkoxy$(C_1-C_4)$alkoxy radicals;
$R_6$ is chosen from a hydrogen atom, a hydroxyl radical, an amino radical, and $(C_1-C_4)$alkyl radicals;
$R_7$ is chosen from a hydrogen atom and $(C_1-C_4)$alkyl radicals;
$R_8$ is chosen from a hydrogen atom, iodine, fluorine, and an amino radical;
$R_9$ is chosen from a hydrogen atom, a hydroxyl radical, an amino radical, $(C_1-C_4)$alkoxy radicals, monohydroxy $(C_1-C_4)$alkoxy radicals, and polyhydroxy$(C_2-C_4)$ alkoxy radicals;
wherein at least two of the radicals $R_5$ to $R_9$ are at least one substituent other than a hydrogen atom,
wherein the at least one coupler is not 2,5-diaminopyridine; and
wherein said composition lacks any enzymatic system capable of oxidizing any of the compounds of formula (I) and/or (II).

16. A process according to claim 15, wherein said keratinous fibers are chosen from human keratinous fibers.

17. A process according to claim 16, wherein said human keratinous fibers are hairs.

18. A process according to claim 15, wherein said oxidizing agent is chosen from hydrogen peroxide, urea hydrogen peroxide, alkali metal bromates, persalts, and peracids.

* * * * *

UNITED STATES PATENT AND TRADEMARK OFFICE
CERTIFICATE OF CORRECTION

PATENT NO. : 6,692,540 B1
DATED : February 17, 2004
INVENTOR(S) : Marie-Pascale Audousset It is certified that error appears in the above-identified patent and that said Letters Patent is hereby corrected as shown below:

Title page,
Item [57], ABSTRACT,
Line 5, "thus" should read -- this --.

Column 8,
Line 42, "a $(C_1-C_4)$alkoxy radicals," should read -- $(C_1-C_4)$alkoxy radicals, --.

Column 9,
Line 65, "in which" should read -- in which: --.

Signed and Sealed this

Twenty-second Day of June, 2004

JON W. DUDAS
*Acting Director of the United States Patent and Trademark Office*